US012090072B2

(12) United States Patent
Raychev et al.

(10) Patent No.: US 12,090,072 B2
(45) Date of Patent: Sep. 17, 2024

(54) SYSTEMS AND METHODS FOR DELIVERY RETRIEVABLE STENTS

(71) Applicant: ICAD ENDOVASCULAR LLC, Fremont, CA (US)

(72) Inventors: Radoslav I. Raychev, Los Angeles, CA (US); Eric P. Stoppenhagen, Round Rock, TX (US); Mark Dias, Round Rock, TX (US)

(73) Assignee: ICAD ENDOVASCULAR LLC, Fremont, CA (US)

( * ) Notice: Subject to any disclaimer, the term of this patent is extended or adjusted under 35 U.S.C. 154(b) by 658 days.

(21) Appl. No.: 16/508,055

(22) Filed: Jul. 10, 2019

(65) Prior Publication Data

US 2020/0146852 A1 May 14, 2020

Related U.S. Application Data

(63) Continuation-in-part of application No. 16/189,596, filed on Nov. 13, 2018, now Pat. No. 10,390,982.

(51) Int. Cl.
*A61F 2/90* (2013.01)
*A61B 17/221* (2006.01)
(Continued)

(52) U.S. Cl.
CPC .................. *A61F 2/88* (2013.01); *A61F 2/90* (2013.01); *A61F 2/966* (2013.01);
(Continued)

(58) Field of Classification Search
CPC ..... A61F 2/01–2/014; A61F 2/86; A61F 2/88; A61F 2/90; A61F 2/95–2/97;
(Continued)

(56) References Cited

U.S. PATENT DOCUMENTS 4,585,000 A * 4/1986 Hershenson .......... A61M 29/02 604/109
4,650,466 A * 3/1987 Luther ........... A61B 17/320725 606/198

(Continued)

FOREIGN PATENT DOCUMENTS

JP 2008539872 A 11/2008
JP 2012510352 A 5/2012

(Continued)

OTHER PUBLICATIONS

U.S. Appl. No. 16/189,596 , Non-Final Office Action, Jan. 17, 2019, 16 pages.

(Continued)

*Primary Examiner* — Kathleen S Holwerda
(74) *Attorney, Agent, or Firm* — Dorsey & Whitney LLP

(57) ABSTRACT

Systems and method for delivering and deploying an expandable stent to treat Intracranial atherosclerotic disease (ICAD) involving large and medium-sized blood vessels. The disclosed systems include a catheter, a shaft comprising a distal end disposed within the catheter, an expandable stent comprising a proximal end and a distal end, wherein the shaft is coupled to the expandable stent and the shaft is disposed within the expandable stent, and a plurality of struts, wherein a first end of each strut is coupled to the shaft and a second end of each strut is coupled to the expandable stent. Longitudinal movement of the shaft relative to the expandable stent extends the plurality of struts radially outward and expands the expandable stent, similar to umbrella. The plurality of struts provides radial force to the expandable stent in an expanded configuration to the vessel walls of the patient.

9 Claims, 8 Drawing Sheets

(51) Int. Cl.

| | |
|---|---|
| ***A61F 2/01*** | (2006.01) |
| ***A61F 2/88*** | (2006.01) |
| ***A61F 2/966*** | (2013.01) |
| *A61B 17/22* | (2006.01) |
| *A61B 18/00* | (2006.01) |
| *A61F 2/82* | (2013.01) |
| *A61F 2/95* | (2013.01) |

(52) U.S. Cl.

CPC ............... *A61B 2017/22001* (2013.01); *A61B 2018/00422* (2013.01); *A61F 2002/823* (2013.01); *A61F 2002/9528* (2013.01); *A61F 2210/0004* (2013.01); *A61F 2250/0059* (2013.01); *A61F 2250/0067* (2013.01)

(58) Field of Classification Search

CPC .......... A61B 17/221; A61B 2017/2217; A61B 17/320725

See application file for complete search history.

(56) References Cited

U.S. PATENT DOCUMENTS

| | | | | |
|---|---|---|---|---|
| 4,921,484 | A * | 5/1990 | Hillstead ............... | A61M 25/10 606/159 |
| 5,002,560 | A * | 3/1991 | Machold .................. | A61F 2/95 606/198 |
| 5,449,372 | A * | 9/1995 | Schmaltz ................. | A61F 2/88 606/198 |
| 5,643,309 | A | 7/1997 | Myler et al. | |
| 6,071,286 | A | 6/2000 | Mawad | |
| 6,120,522 | A | 9/2000 | Vrba et al. | |
| 6,468,298 | B1 | 10/2002 | Pelton | |
| 6,551,342 | B1 * | 4/2003 | Shen ..................... | A61F 2/0105 606/200 |
| 6,575,959 | B1 | 6/2003 | Sarge et al. | |
| 7,004,962 | B2 | 2/2006 | Stinson | |
| 7,037,330 | B1 | 5/2006 | Rivelli et al. | |
| 7,294,137 | B2 | 11/2007 | Rivelli et al. | |
| 7,468,070 | B2 | 12/2008 | Henry et al. | |
| 8,092,508 | B2 | 1/2012 | Leynov et al. | |
| 8,197,493 | B2 | 6/2012 | Ferrera et al. | |
| 8,506,615 | B2 | 8/2013 | Leynov et al. | |
| 8,758,364 | B2 | 6/2014 | Eckhouse et al. | |
| 8,795,317 | B2 | 8/2014 | Grandfield et al. | |
| 8,864,792 | B2 | 10/2014 | Eckhouse et al. | |
| 9,005,237 | B2 | 4/2015 | Eckhouse et al. | |
| 9,034,008 | B2 | 5/2015 | Eckhouse et al. | |
| 9,561,121 | B2 | 2/2017 | Sudin et al. | |
| 9,682,216 | B2 | 6/2017 | Teitelbaum | |
| 9,808,359 | B2 | 11/2017 | Ferrera et al. | |
| 9,844,381 | B2 | 12/2017 | Eckhouse et al. | |
| 9,968,360 | B2 | 5/2018 | Stoppenhagen et al. | |
| 10,022,251 | B2 | 7/2018 | Teitelbaum | |
| 10,265,204 | B2 * | 4/2019 | Ide ....................... | A61L 31/148 |
| 2003/0144731 | A1 | 7/2003 | Wolinksky et al. | |
| 2004/0158307 | A1 | 8/2004 | Jones et al. | |
| 2005/0033410 | A1 | 2/2005 | Hogendijk et al. | |
| 2005/0288763 | A1 | 12/2005 | Andreas et al. | |
| 2006/0184226 | A1 | 8/2006 | Austin | |
| 2006/0259119 | A1 | 11/2006 | Rucker | |
| 2007/0208367 | A1 * | 9/2007 | Fiorella .................. | A61B 17/22 606/198 |
| 2008/0269868 | A1 | 10/2008 | Bei et al. | |
| 2010/0331951 | A1 | 12/2010 | Bei et al. | |
| 2011/0009875 | A1 * | 1/2011 | Grandfield ........... | A61B 17/221 606/127 |
| 2011/0009945 | A1 | 1/2011 | Parker et al. | |
| 2011/0077731 | A1 | 3/2011 | Lee et al. | |
| 2011/0152920 | A1 | 6/2011 | Eckhouse et al. | |
| 2011/0160742 | A1 | 6/2011 | Ferrera et al. | |
| 2011/0160761 | A1 | 6/2011 | Ferrera et al. | |
| 2011/0202088 | A1 | 8/2011 | Eckhouse et al. | |
| 2012/0130480 | A1 * | 5/2012 | Falotico .................. | A61L 31/16 623/1.42 |
| 2013/0030460 | A1 * | 1/2013 | Marks .................. | A61B 17/221 606/200 |
| 2013/0238079 | A1 * | 9/2013 | Bingener-Casey ....... | A61F 2/90 623/1.2 |
| 2013/0245742 | A1 * | 9/2013 | Norris ....................... | A61F 2/07 623/1.11 |
| 2013/0325055 | A1 | 12/2013 | Eckhouse et al. | |
| 2013/0325056 | A1 | 12/2013 | Eckhouse et al. | |
| 2014/0243885 | A1 | 8/2014 | Eckhouse et al. | |
| 2014/0257362 | A1 * | 9/2014 | Eidenschink ............. | A61F 2/01 606/200 |
| 2014/0364896 | A1 * | 12/2014 | Consigny ........... | A61B 17/3207 606/200 |
| 2015/0100113 | A1 * | 4/2015 | Davidson .................. | A61F 2/90 623/1.11 |
| 2015/0313732 | A1 * | 11/2015 | Fulton, III ................ | A61F 2/82 623/1.11 |
| 2015/0327866 | A1 | 11/2015 | Eckhouse et al. | |
| 2017/0340330 | A1 | 11/2017 | Stoppenhagen | |
| 2018/0028209 | A1 | 2/2018 | Sudin et al. | |
| 2018/0049859 | A1 | 2/2018 | Stoppenhagen et al. | |
| 2018/0055666 | A1 | 3/2018 | Ferrera et al. | |
| 2019/0015142 | A1 * | 1/2019 | Mitchell ................. | A61L 31/14 |

FOREIGN PATENT DOCUMENTS

| | | | |
|---|---|---|---|
| WO | 2006119144 | A1 | 11/2006 |
| WO | 2011082319 | A1 | 7/2011 |
| WO | 2017127692 | A1 | 7/2017 |
| WO | 2018169959 | A1 | 9/2018 |

OTHER PUBLICATIONS

U.S. Appl. No. 16/189,596 , Notice of Allowance, May 22, 2019, 8 pages.

* cited by examiner 302
402
$\theta_1$
410
410
400
310
300

402
302
$\theta_2$
400
410
412
411
410
404
310
300

SYSTEMS AND METHODS FOR DELIVERY RETRIEVABLE STENTS

RELATED CASES

This application is a continuation-in-part of U.S. application Ser. No. 16/189,596, filed on Nov. 13, 2018, and titled "SYSTEMS AND METHODS FOR DELIVERY RETRIEVABLE STENTS," which is hereby incorporated by reference herein in its entirety.

BACKGROUND

The present disclosure relates generally to the field of endovascular treatment of blood vessels. More particularly, some embodiments relate to endovascular treatment of hemodynamically significant intracranial atherosclerotic disease (ICAD).

SUMMARY

Intracranial atherosclerotic disease (ICAD) involving large and medium-sized blood vessels is the leading cause of ischemic stroke worldwide with an estimated occurrence up to 50 percent. It is a predominately prevalent in Asia, South America, and the Middle East and less commonly encountered in Europe and North America. It accounts for 8-10 percent of all ischemic strokes in North America, and 30-50 percent in Asia. The three main mechanisms leading to ischemic stroke due to ICAD are hypoperfusion, branch atheromatous disease, and artery-to-artery embolism.

Current endovascular therapy for ICAD in acute and subacute settings is very limited due to suboptimal current technology, limited ability for balloon angioplasty due to high chance of re-occlusion, and need of permanent stent implantation.

The present disclosure proposes a novel approach to endovascular treatment of hemodynamically significant ICAD, aimed to achieve adequate revascularization without the complications associated with the currently available technology, which involved placement of occlusive balloon for angioplasty and implantation of a permanent stent. This method and design allow for both temporary and prolonged deployment of retrievable stents with an adjustable radial force. Additionally, the present application allows for continuous flow and parent vessel conformability as an attractive alternative to balloon angioplasty and stenting.

BRIEF DESCRIPTION OF THE DRAWINGS

The written disclosure herein describes illustrative embodiments that are non-limiting and non-exhaustive. Reference is made to certain of such illustrative embodiments that are depicted in the figures.

DETAILED DESCRIPTION

Figure 1:
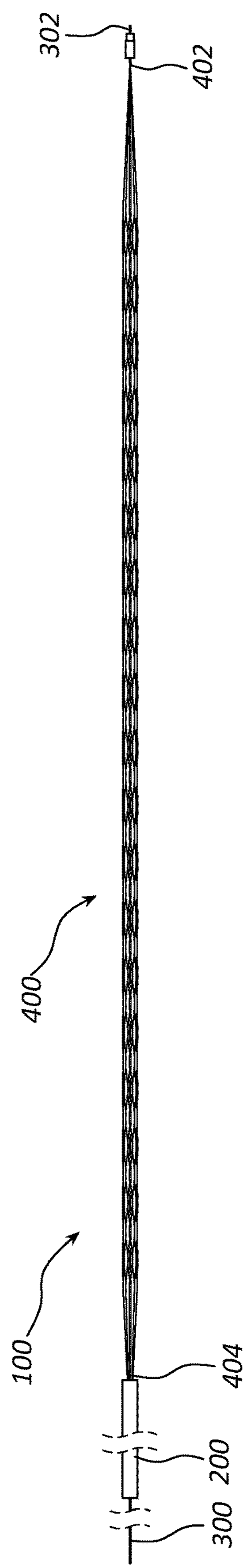
FIG. 1 shows an expandable stent in a collapsed configuration according to one embodiment.

The natural history of ICAD derived from randomized data involving medical therapy demonstrated that recurrent stroke rate is proportional to the degree of stenosis with very high risk in the severe (>70%) category. These data prompted the first randomized clinical trial SAMMPRIS comparing angioplasty and stenting against best medical therapy (dual antiplatelet therapy with ASA and Plavix, statin with LDL goal<1=70 mg/dl, and SBP goal <130/80)). The results of the trial showed much worse (23%) risk of stroke after percutaneous angioplasty and stenting (PTAS) with the Wingspan system as compared with best medical therapy (15%). Another trial called VISSIT involving balloon-mounted stent demonstrated very similar results to SAMMPRIS. However, despite the superiority of medical over endovascular therapy, both trials clearly demonstrated that substantial number of patients remain at high risk of stroke while being treated with aggressive medical management. This failure of medical therapy in ICAD can be explained by inadequate selection of the appropriate treatment, based on careful consideration of each of above listed different pathophysiologic mechanisms. Patients with severe stenosis associated with distal hemodynamic compromise and poor collaterals are at highest risk of recurrent ischemic stroke and logically less likely to benefit from antiplatelet and lipid lowering therapy. A post hoc analysis of the medical arm of SAMMPRIS trial showed that the most common pattern of infarction was border-zone (52.4%), followed by territorial (23.8%), and perforator (23%). Patients who had borderzone infarcts were more likely to have poor collaterals, and had a higher risk of recurrent stroke. Thus, the current data provides compelling evidence that patients with severe intracranial stenosis associated with distal hypoperfusion are at highest risk of recurrent stroke, despite best medical therapy and those patients may benefit from endovascular revascularization. This notion is supported by evidence from Chinese stenting registry, which demonstrated low periprocedural risk in patients with severe hypoperfusion, short segment lesions and who were treated within 3 weeks of the qualifying event. Similar results were achieved in the recently completed WEAVE single arm trial, which enrolled patients who fit only the current FDA recommendations for intracranial PTAS with the Wingspan system (proven failure of medical therapy and treatment after minimum of 7 days of qualifying event). Both studies involved rigorous patient selection with focal Mori type A lesions and prolonged treatment time after stroke and demonstrated superior results as compared to SAMMPRIS and VISSIT. However, these limitations significantly restrict the applicability of the PTAS as they apply to only a fraction of the ICAD patients with severe stenosis. Thus, the current endovascular revascularization for ICAD is limited only to patients who fail medical therapy and only after 7 days of TIA or stroke. Moreover, the only device approved on the US market is Wingspan/Gateway balloon system, which is an outdated technology requiring complicated exchange process. Given its design (self-expanding, high radial force with strong vessel straightening effect), the device is also useful only for focal short-segment stenosis (Mori type A), and does not work well in more extensive plaques (Mori Type b and c) and tortuous intracranial anatomy.

In addition to the less strict patient selection, the reasons for failed PTAS have been attributed to both technical (vessel rupture and wire perforation), and medical factors (plaque snow-plowing effect with perforator occlusion, and delayed intraparenchymal hemorrhage.

Perforator occlusion after stenting: Unlike the coronary and peripheral vessels, the intracranial vessel affected by ICAD have multiple tiny perforators (80-400 microns) arising from the sidewall and feeding important subcortical structures. Inflation of balloon, followed by permanent stenting results in "snow-plowing" of the plaque against the vessel wall, which is associated with risk of occlusion of these perforators and consequent subcortical stroke. (Table 1 highlights differences between intracranial and coronary vessels).

Hemorrhagic transformation of ischemic infarct: The infarcted brain parenchyma is particularly sensitive to hemorrhagic transformation, particularly in setting of reperfusion and dual antiplatelet therapy (DAPT), required for any permanent stent implantation.

Vessel rupture. As noted above, the tortuous intracranial vessels are particularly prone to dissection, due to lack of external elastic lamina and poor tissue support. Dissections can be caused by aggressive and repetitive balloon angioplasty in setting of re-occlusions and severe elastic recoil. Wire perforation is another important factor, particularly in setting of exchange process required for the Wingspan system. The cervical and intracranial tortuosity of ICAD patients leads to inevitable wire instability during the exchange process with consequent risk of vessel rupture due to distal wire tip displacement.

Delayed thrombosis and restenosis. These are common complications of any permanent stent implantation with an estimated symptomatic rate in ICAD of up to 14%.

TABLE 1

Important differences between Intracranial vessels and coronary vessels:

| Features | MCA | LAD |
|---|---|---|
| External elastic membrane | Absent | Present |
| Diameter | 3.71-2.41 mm | 4.5-2.5 mm |
| Wall thickness | 0.094 ± 0.03 mm | 0.87 ± 0.23 mm |
| Dominating wall component | Media | Adventitia |
| Stiffness | ++ | + |
| Tissue support | + | ++++ |
| Branching vessels supplying eloquent tissue | +++++ | + |

Angioplasty alone has been historically considered as the initial endovascular therapy of ICAD and recently re-emerged as an alternative to permanent stent implantation. Multiple case series and studies have suggested that angioplasty alone without permanent stenting may be a viable option for severe ICS with hemodynamic compromise. However, the unpredictable degree of elastic recoil is a common drawback, leading to immediate re-occlusion and also high risk of subacute re-stenosis due to intimal hyperplasia. One of the cited methods to prevent dissection, and re-occlusion is prolonged inflation. However, in the intracranial vasculature this technique carries high risk of cerebral ischemia due to prolonged vessel occlusion.

Another limitation of the current technology (Gateway balloon) is that the delivery and deployment requires and exchange over a microwire which is usually positioned in M2/M3 segment. As noted above, this exchange process is an independent risk of intracranial vessel perforation due to high likelihood of wire instability in setting of tortuosity and atherosclerotic disease in the proximal vasculature often seen in this patient population.

Furthermore, despite the proven benefit of thrombectomy for treatment of acute ischemic stroke (AIS) due to large vessel occlusion (LVO), the currently available devices are effective in retrieving clots of proximal embolic source, rather than in-situ atherothrombi. This limitation is particularly relevant to the Asian population where the ICAD is the leading cause of ischemic stroke.

Another important limitation of acute revascularization in setting of acute large vessel occlusion (LVO) due to underlying ICAD is the need of rescue stenting after failed thrombectomy, with associated 17-20% risk of symptomatic intracranial hemorrhage.

As such, the current endovascular therapy for ICAD in acute and subacute setting is very limited due to suboptimal current technology, limited ability for balloon angioplasty due to high chance of re-occlusion, and need of permanent stent implantation.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, fluidic, and thermal interaction. Thus, two components may be coupled to each other even though they are not in direct contact with each other. The phrases "attached to" or "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end or the end nearest the practitioner during ordinary use.

The present disclosure is directed to expandable stents. The expandable stents may fall within a number of different categories, such as laser cut stents that are cut from a hypotube and a braided stents that comprise woven individual wires. FIG. 1 illustrates a retrievable expandable stent delivery system 100 for endovascular treatment of hemodynamically significant intracranial atherosclerotic disease (ICAD). The retrievable expandable stent delivery system 100 includes a catheter 200, a shaft 300, and an expandable stent 400. The shaft 300 and the expandable stent 400 may be disposed within the catheter 200. The catheter 200 may be a microcatheter and have an internal diameter that ranges of 0.017 inches to 0.021 inches. The shaft 300 and the expandable stent 400 may be configured to slidably advance within the catheter 200. In some embodiments, the catheter 200 and the shaft 300 may be coupled to a handle (not shown) that may enable a user to manipulate the catheter 200, the shaft 300, and the expandable stent 400 coupled to the shaft 300.

In some embodiments, the shaft 300 may include an internal lumen. The internal lumen of the shaft 300 may enable the retrievable expandable stent delivery system 100 to be advanced over a guidewire (not shown) that was previously advanced to a target location. The shaft 300 comprises a distal end 302. The distal end 302 of the shaft 300 may have a rounded tip that may help prevent vessel perforation during the procedure.

In some embodiments, the retrievable expandable stent 400 may be coupled to the shaft 300. For example, a distal end 402 of the expandable stent 400 may be coupled to the distal end 302 of the shaft 300. A proximal end 404 of the expandable stent 400 may be coupled to a collar 406 that is configured to encompass the shaft 300. The collar 406 may be configured to slide longitudinally over the shaft 300. In some embodiments, the collar 406 may be locked in a specific location position relative to the shaft 300, enabling the distal end 402 of the expandable stent 400 to move relative to the proximal end 404. The relative movement between the distal end 402 and the proximal end of the expandable stent 400 may be controlled by the handle previously described that may be manipulated by the user.

Figure 2:
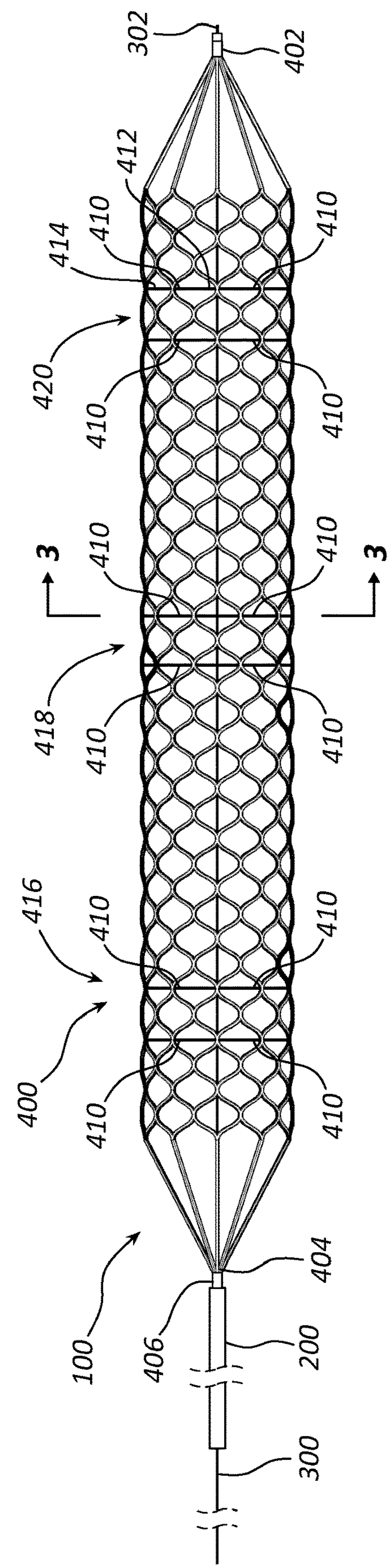
FIG. 2 shows the expandable stent of FIG. 1 in an expanded configuration.

In some embodiments, the relative movement between the distal end 402 and the proximal end 404 of the expandable stent 400 is configured to expand the expandable stent 400. FIG. 1 illustrates the expandable stent 400 in a collapsed configuration and FIG. 2 illustrates the expandable stent 400 in an expanded configuration. Similarly, the relative movement between the distal end 402 and the proximal end 404 may also collapse the expandable stent 400 after the procedure is completed.

In some embodiments, the expandable stent 400 may be fabricated from a memory material, such as Nitinol, and the expandable stent 400 may be in the collapsed configuration when the expandable stent 400 is sheathed by the catheter 200. The expandable stent 400 may expand when the expandable stent 400 is unsheathed from the catheter 200 enabling the expandable stent 400 to expand to a predetermined shape. Unsheathing may occur by either advancing the expandable stent 400 from the catheter 200 or by retracting the catheter 200 from the expandable stent 400. The expandable stent 400 may be collapsed after the procedure is finished by resheathing the expandable stent 400. Resheathing may occur by retracting the expandable stent 400 back into the catheter 200 or by advancing the catheter 200 over the expandable stent 400.

FIG. 2 illustrates the retrievable expandable stent delivery system 100 with the expandable stent 400 in the expanded configuration. The expandable stent 400 may have a plurality of different design components. The illustrated embodiment of FIG. 2 shows a central region of the expandable stent 400 with a tubular straight shape and a plurality of closed cells.

In some embodiments, the stent may have a tapered configuration. For example, the stent may taper from a proximal end of the stent to a distal end of the stent. In another embodiment, the stent may taper from a distal end to a proximal end of the stent. In another embodiment, the stent may taper in opposite directions from the center of the stent. For example, the stent may taper from the center of the stent to a distal end of the stent and may taper in the opposite direction from the center of the stent to the proximal end of the stent.

In some embodiments, the stent may have a plurality of closed cells rather than a plurality of open cells. In other embodiments, the cells of the stent may be a hybrid cell design that includes a plurality of closed cells and a plurality of open cells. The cell design may be manufactured in a number of methods, such as laser cutting, etc. In some embodiments, the expandable stent 400 may have a braided design. Braided (or alternative) designs with approximately 30 percent porosity allow adequate plaque coverage without perforator vessel occlusion. The braided technology also allows more flexibility and conformability to the parent vessel, which is a typical characteristic of intracranial vasculature.

In some embodiments, an outer surface of the expandable stent 400 may have a porosity that ranges from 10 to 35 percent. In some embodiments, the expandable stent 400 may have a porosity that ranges from 15 to 30 percent.

In the illustrated embodiment of FIG. 2, the expandable stent 400 may further include a plurality of struts 410 that are configured to help expand the expandable stent 400 from the collapsed configuration to the expanded configuration. A first end 412 of each strut 410 may be coupled to the shaft 300 and a second end 414 of each strut 410 may be coupled to the expandable stent 400. Longitudinal movement of the shaft 300 relative to the expandable stent 400 may extend radially outward the plurality of struts 410 and expand the retrievable expandable stent 400 from the collapsed configuration to the expanded configuration. The struts 410 are configured to help maintain the shape of the expandable stent 400 in the expanded configuration.

The plurality of struts 410 may be disposed longitudinally along the shaft 300 between the distal end 402 and the proximal end 404 of the expandable stent 400. The struts 410 may be equally spaced along the shaft 300, or the struts 410 may not be equally spaced along the shaft 300. In some embodiments, the struts 410 may be disposed in subsets along the shaft 300. For example, FIG. 2 illustrates several subsets, a first subset 416 of struts disposed in a proximal portion, a second subset 418 of struts disposed in a central portion, and third subset 420 of struts disposed in a distal portion of the expandable stent 400.

Figure 3:
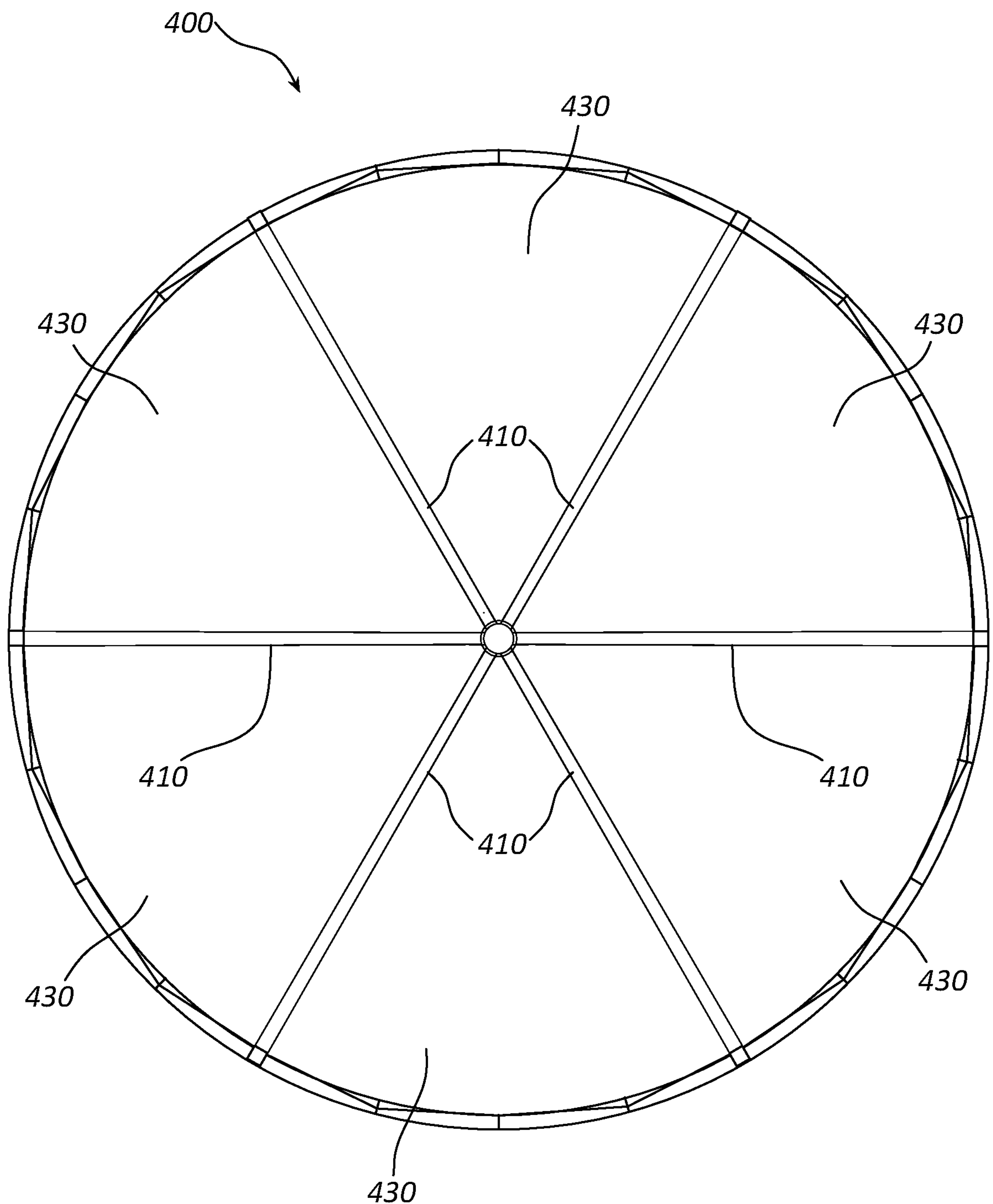
FIG. 3 shows a cross-sectional view of the expandable stent of FIG. 2.

In some embodiments, struts 410 may be radially spaced apart around the shaft 300. This is illustrated in FIG. 3, which is a cross-sectional view of the retrievable expandable stent delivery system 100 taken along cross-sectional line 3-3 shown in FIG. 2. FIG. 3 illustrates a plurality of struts 410 that are radially spaced around the shaft 300. In illustrated embodiments, the struts 410 may be equally spaced around the shaft 300. In other embodiments, the struts 410 may not be equally spaced around the shaft 300. FIG. 3 illustrates six struts 410; however, the present disclosure is not so limited, and there may be more or fewer than six struts. There may be as few as three struts 410 disposed around the shaft 300 and as many as 10 struts disposed around the shaft 300 in a single subset of struts 410.

In some embodiments, the struts 410 that are disposed along the shaft 300 may be radially aligned with the other struts 410 that are disposed along the shaft 300. For example, the first subset 416, the second subset 418, and the third subset 420 may each include a plurality of struts 410 that are disposed around the shaft 300 and are radially aligned with each other. The radial alignment of the struts may create a plurality of channels 422 that extend from the distal end 402 to the proximal end 404 of the expandable stent 400. The channels 422 may enable blood flow or perfusion of blood through the expandable stent 400 in the expanded configuration.

In some embodiments, the longitudinal length of the expandable stent 400 in the expanded configuration may range between 5 mm and 30 mm.

Figure 4:
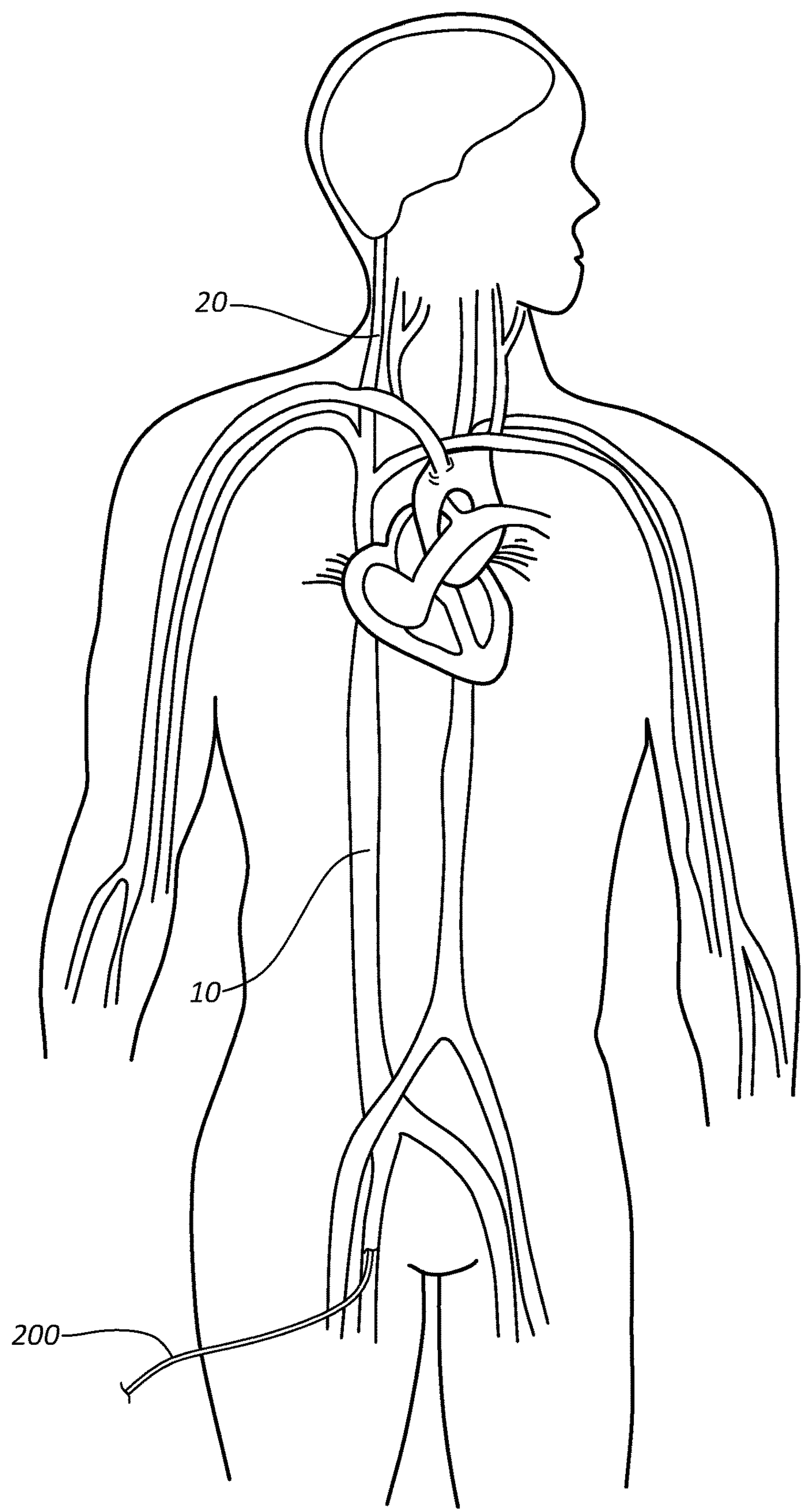
FIG. 4 shows an illustration of an anatomical path of travel of an expandable stent system.

FIG. 4 shows an illustration of an anatomical path of travel of the retrievable expandable stent delivery system 100. The catheter 200 may be inserted into a femoral artery of a patient (using, for example, the Seldinger technique) and advance up through an aorta 10 of the patient, from there the catheter 200 may be advanced up through a carotid artery 20 to an intracranial target location. FIG. 4 illustrates an intracranial target location; however, other vasculature target locations be targeted within the patient's vasculature. The target location may be a partially occluded or fully occluded vessel that may be treated with the retrievable expandable stent delivery system 100. Once the catheter 200 has reached the target location, the shaft 300 and the expandable stent 400 may be advanced out of the catheter 200. The expandable stent 400 may be expanded and the stent may come in contact with plaque disposed on the vessel walls, and the expandable stent 400 may crush or crack the plaque via the adjustable radial force of the expandable stent 400. The expandable stent 400 may be deployed (expanded) at the target location for a prolonged period of time (up to 30 minutes), allowing the vessel patency and distal antegrade flow. The expandable stent 400 may be deployed in blood vessels that have a diameter between 1.5 mm and 7 mm.

In certain embodiments, the expandable stent 400 in the expanded configuration has the ability to maintain vessel patency for 15-30 minutes while the radial force of the expandable stent 400 keeps the plaque from re-coiling, minimizing the elastic recoil and risk of re-occlusion after retrieval of the expandable stent 400. The porosity of the expandable stent 400 minimizes the risk of perforator occlusion and snow-plowing compared to balloons, which cover the plaque uniformly.

In some embodiments, the expandable stent 400 may be detached from the shaft 300 and left in the target area for prolonged treatment. The expandable stent 400 may be detached through a mechanical detachment or electrolytic, thermo mechanical, or other detachment mechanism at a detachment region, which may correspond with the proximal end 404 of the expandable stent 400.

The expandable stent 400 may be radiopaque or may comprise a plurality of radiopaque markers that may enable a user or medical professional to see the retrievable expandable stent delivery system 100 using medical imaging.

Figure 5:
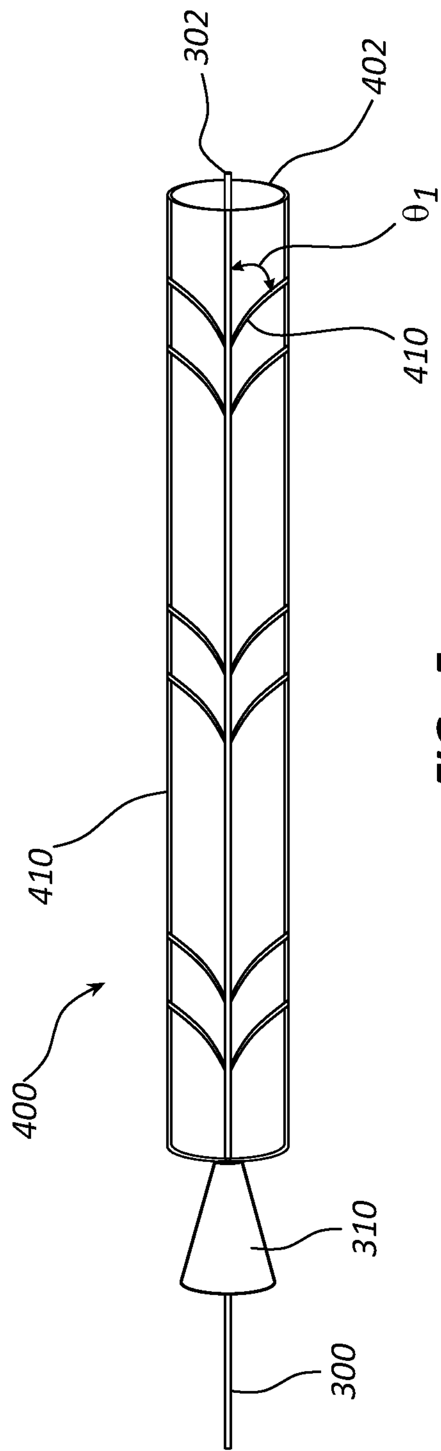
FIG. 5 is a schematic representation of an expandable stent comprising a plurality of struts, according to one embodiment, the expandable stent in a collapsed or semi-collapsed configuration.
Figure 6:
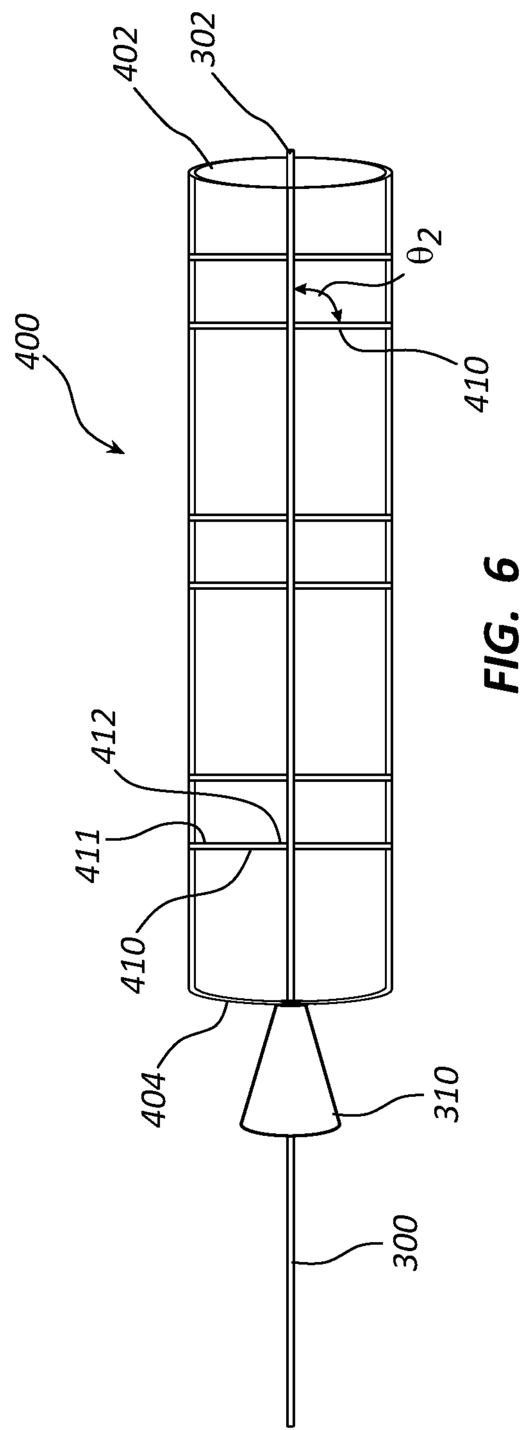
FIG. 6 is a schematic representation of the expandable stent of FIG. 5 in an expanded configuration.

FIGS. 5 and 6 are schematic representations of the deployment and expansion of the expandable stent 400. The expandable stent 400 opens radially like an umbrella. FIG. 5 illustrates the expandable stent 400 in the collapsed or semi-collapsed configuration. In the collapsed or semi-collapsed configuration, the struts 410 are angled relative to the shaft 300 at an angle $\theta_1$. In some embodiments, the angle $\theta_1$ may range between 0 and 15 degrees in the collapsed configuration. In some embodiments, the angle $\theta_1$ may range between 0 and 75 degrees in the semi-collapsed configuration FIG. 5 illustrates the struts 410 oriented in a distal direction. Resheathing of the stent may be facilitated when the plurality of struts are oriented in the distal direction. In some embodiments, the struts 410 may be oriented in a proximal direction.

A user may expand the expandable stent 400 to the expanded configuration, as illustrated in FIG. 6, by extending the plurality of struts 410 radially outward, which expands the expandable stent 400. In the expanded configuration, the struts 410 may be angled relative to the shaft 300 at an angle $\theta_2$. In some embodiments, the angle $\theta_2$ may range between 45 and 90 degrees. In some embodiments, the angle $\theta_2$ may range between 75 and 90 degrees. The angle $\theta_2$ determines that amount of radial force that is applied to the expandable stent 400 in the expanded configuration. The closer the angle $\theta_2$ is to 90 degrees the more radial force the struts 410 apply to the expandable stent 400. This enables a user to apply an adjustable radial force to the outer surface of the expandable stent 400 that changes relative to the angle of the struts relative to the shaft 300. For example, the smaller the angle the smaller the radial force and the larger the angle the large the radial force up to 90 degrees. Accordingly, the user may control the amount of radial force applied to the vessel walls of a patient by controlling the movement of the shaft 300 and the radial outward movement of the plurality of struts 410. The struts 410 may apply between 0.00590 and 0.0090 Newtons/mm of radial force.

As discussed previously, the distal end 302 of the shaft 300 may be coupled to the distal end 402 of the expandable stent 400. The shaft 300 may comprise a locking mechanism 310 that is configured to prevent movement of the proximal end 404 of the expandable stent 400 relative to the shaft 300. The locking mechanism may be achieved via a handle locking the shaft 300 relative to the catheter 300.

The expandable stent 400 may be expanded from the collapsed configuration to the expanded configuration by moving the distal end 402 of the expandable stent 400 toward the proximal end 404 of the expandable stent 400. This may be accomplished by engaging the locking mechanism 310 and preventing movement of the distal end 402 of the expandable stent 400. Similarly, the expandable stent 400 may be collapsed from the expanded configuration to the collapsed configuration by moving the distal end 402 of the expandable stent 400 away from the proximal end 404 of the expandable stent 400.

The expandable stent 400 may be expanded by applying a proximally oriented force (pulling) to the shaft 300. The distal end 302 of the shaft 300 is coupled to the distal end 402 of the expandable stent 400 and the distal end 402 of the expandable stent 400 is pulled toward the proximal end 404 of the expandable stent 400. The proximal end 404 of the expandable stent 400 is locked in positon via the locking mechanism 310 and prevents movement of the proximal end 404 when the proximally oriented force is applied to the shaft 300. The reverse movement would collapse the expandable stent 400 from the expanded configuration to the collapsed configuration.

As illustrated in FIG. 5, the expandable stent 400 may also be expanded by applying a distally oriented force (pushing) to the expandable stent 400. In this configuration, the distal end 302 of the shaft 300 and the distal end 402 of the expandable stent 400 are coupled together. The expandable stent 400 may be coupled to an outer shaft that encompasses the shaft 300 and a user may apply the distally oriented force to the outer shaft to move the proximal end 404 of the expandable stent 400 toward the distal end 402 of the expandable stent 400.

Figure 7:
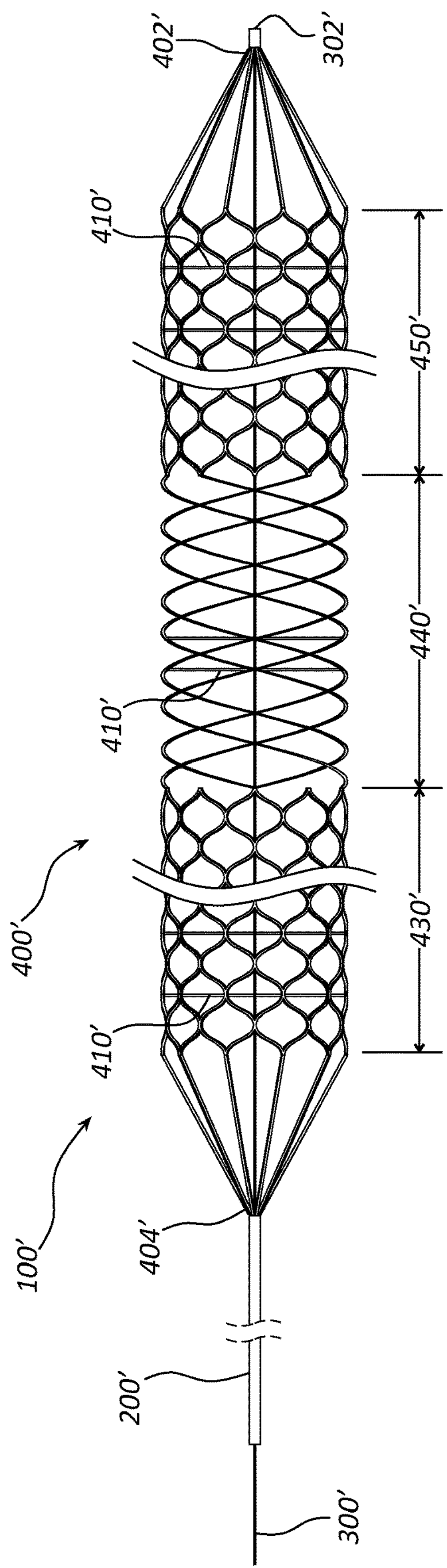
FIG. 7 shows an expandable stent in an expanded configuration, the expandable stent comprises a proximal section, a central section, and a distal section, each with a distinct stent design according to one embodiment.

FIG. 7 depicts an embodiment of a retrievable expandable stent delivery system 100' that resembles the retrievable expandable stent delivery system 100 described above in certain respects. Accordingly, like features are designated with like reference numerals with apostrophes added. For example, the embodiment depicted in FIG. 7 includes a shaft 300' that may, in some respects, resemble the shaft 300 of FIGS. 1-3 and 5-6. Relevant disclosure set forth above regarding similarly identified features thus may not be repeated hereafter. Moreover, specific features of the retrievable expandable stent delivery system 100 and related components shown in FIGS. 1-3 and 5-6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the retrievable expandable stent delivery system 100' and related components depicted in FIG. 7. Any suitable combination of the features, and variations of the same, described with respect to the retrievable expandable stent delivery system 100 and related components illustrated in FIGS. 1-3 and 5-6 can be employed with the retrievable expandable stent delivery system 100' and related components of FIG. 7, and vice versa. This pattern of disclosure applies equally to further embodiments depicted in subsequent figures and described hereafter, wherein the apostrophes may be further incremented.

FIG. 7 illustrates a retrievable expandable stent delivery system 100' that comprises a catheter 200', a shaft 300', and an expandable stent 400'. The expandable stent 400' may include a proximal portion 430', a central portion 440', and a distal portion 450'. Each portion may have a distinct design configuration. For example, the proximal portion 430' and the distal portion 450' comprises a plurality of closed cells. The central portion 440' may include a helical section that comprises a plurality of helical wires that rotate around the shaft 300'. The helical section may provide additional flexibility for the expandable stent 400' to help enable the expandable stent 400' conform or adapt to the blood vessel curvature without too much vessel straightening effect and minimal plaque or vessel injury.

Figure 8:
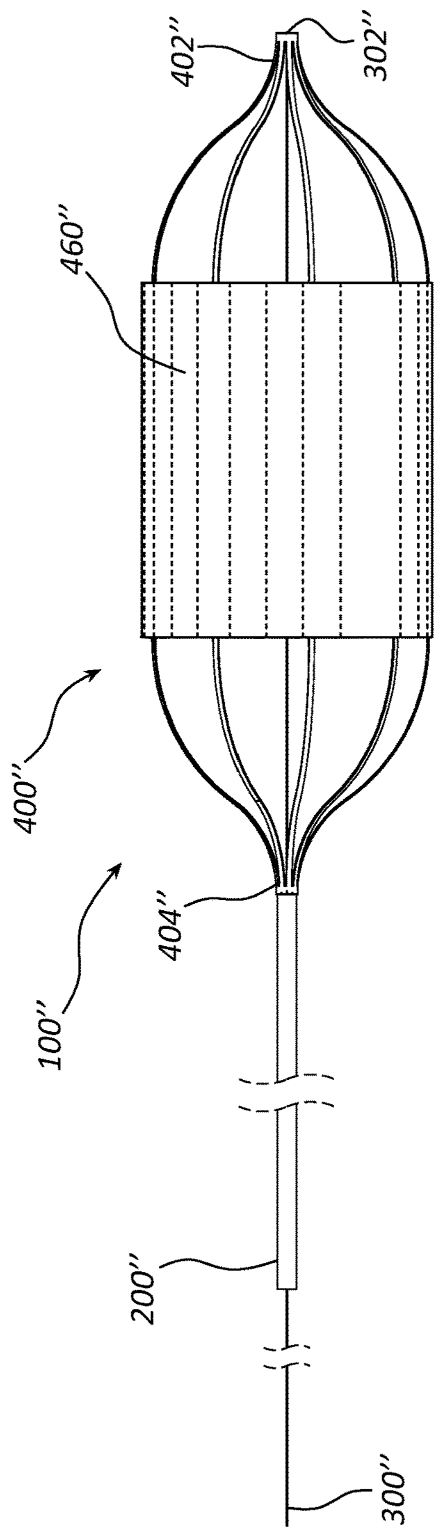
FIG. 8 shows an expandable stent in an expanded configuration, the expandable stent comprises a cover according to one embodiment.

FIG. 8 illustrates a retrievable expandable stent delivery system 100" that comprises a catheter 200", a shaft 300", and an expandable stent 400". The expandable stent 400" may comprise a porous cover 460". The cover 460" may be fine braided mesh, electrospun PTFE, laser cut urethane, porous nitinol thin film, or other suitable materials.

In some embodiments, the cover 460" may have a hydrophilic surface that helps minimize thrombogenicity. In some embodiments, the expandable stent 400" may have a hydrophilic surface, such as a hydrophilic coating that helps minimize thrombogenicity.

Figure 9:
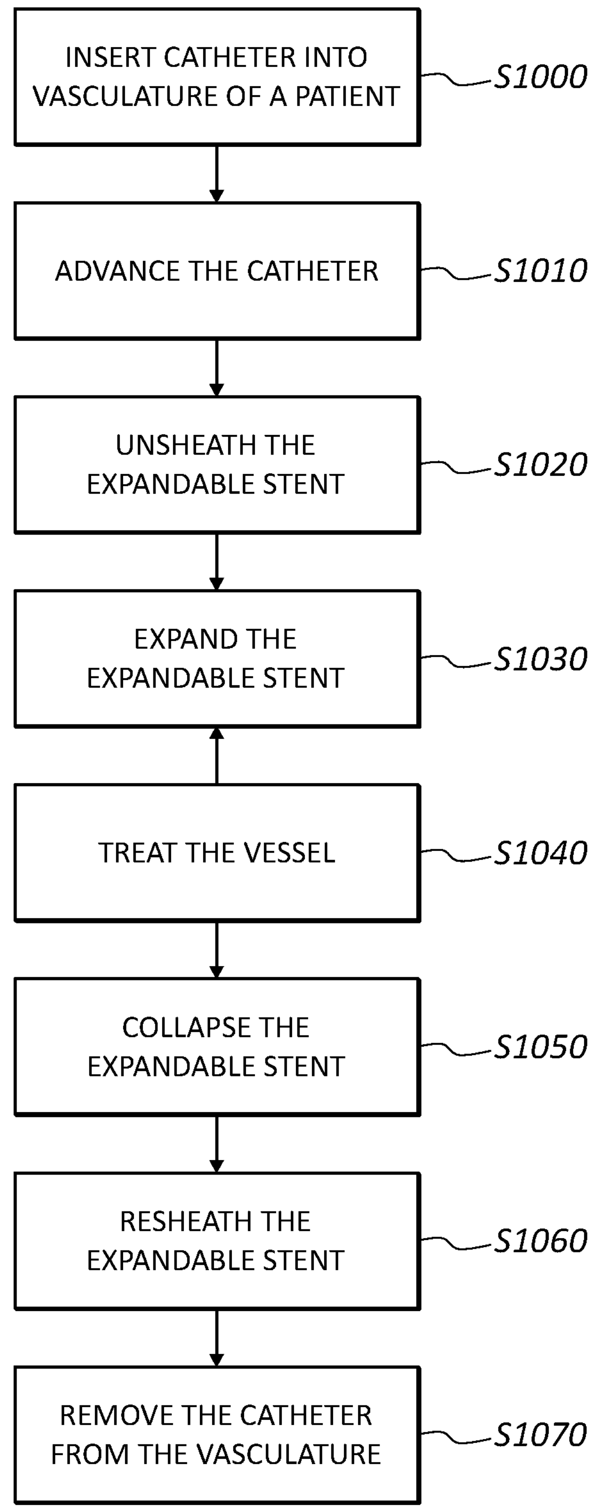
FIG. 9 shows a method of deploying an expandable stent in a patient's vasculature according to one embodiment.

FIG. 9 shows a method of deploying the expandable stent 400 in the vasculature of a patient. Step S1000 describes inserting the catheter 200 into the vasculature of the patient. As previously discussed, the catheter 200 may be inserted into a femoral artery of the patient (using, for example, the Seldinger technique). The catheter 200, however, may be inserted into various different locations of the patient's vasculature. Step S1010 describes advancing the expandable catheter 200 to a target location. FIG. 4 illustrates advancing up through the aorta 10 of the patient; from there the catheter 200 may be advanced up through a carotid artery 20 to an intracranial target location. Other vasculature target locations are within the scope of these disclosure and be anywhere within the patient's vasculature.

Step S1020 describes unsheathing the expandable stent 400 from the catheter 200. This may be accomplished by advancing the expandable stent 400 out of the catheter 200 or by retracting the catheter 200 from the expandable stent 400.

Step S1030 describes expanding the expandable stent 400. As previously described, the expandable stent 400 may expand because it is fabricated from a memory material, such as Nitinol, or the expandable stent 400 may expand via relative movement of the distal end 402 of the expandable stent 400 toward the proximal end 404 of the expandable stent 400. This movement may occur by an umbrella-like movement, by pulling the shaft 300 and extending the plurality of struts 410 radially outward to expand the expandable stent 400.

Step S1040 describes treating the vessel in the target location of the patient. Treatment relies on expanding the expandable stent 400 and crushing or cracking the plaque in the target location. The struts 410 provide an adjustable radial force to crack or crush the plaque and to maintain the shape of the expandable stent 400. The amount of radial force applied by the expandable stent is adjustable and may be controlled by the user. As previously discussed, the relative angle of the plurality of struts 410 relative to the shaft 300 determines the amount of force applied by the outer surface of the expandable stent 400. The smaller the angle the smaller the radial force and the larger the angle the higher the radial force up to 90 degrees. Treatment of the vessel may occur for a predetermined amount of time (up to 30 minutes) or the expandable stent 400 may be detached from the shaft 300 and left in place for a prolonged period to be possibly retrieved later.

Step S1050 describes collapsing the expandable stent 400 to its collapsed configuration after the treatment has been performed. Once the expandable stent 400 is in its collapsed configuration, the expandable stent 400 may be resheathed as described in step S1060. The expandable stent 400 may be resheathed by retracing the expandable stent 400 within the catheter 200 or by advancing the catheter 200 over the expandable stent 400.

Step 1070 describes removing the catheter 200 from the patient's vasculature after the treatment of the vessel has been completed.

Figure 10:
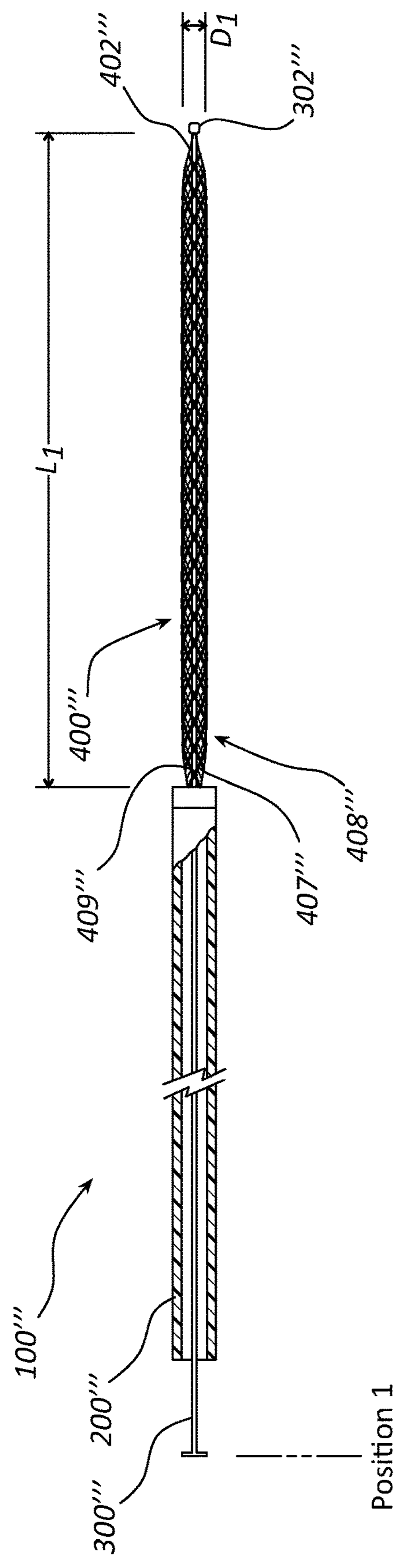
FIG. 10 shows an expandable braided stent in a collapsed configuration, according to one embodiment.
Figure 11:
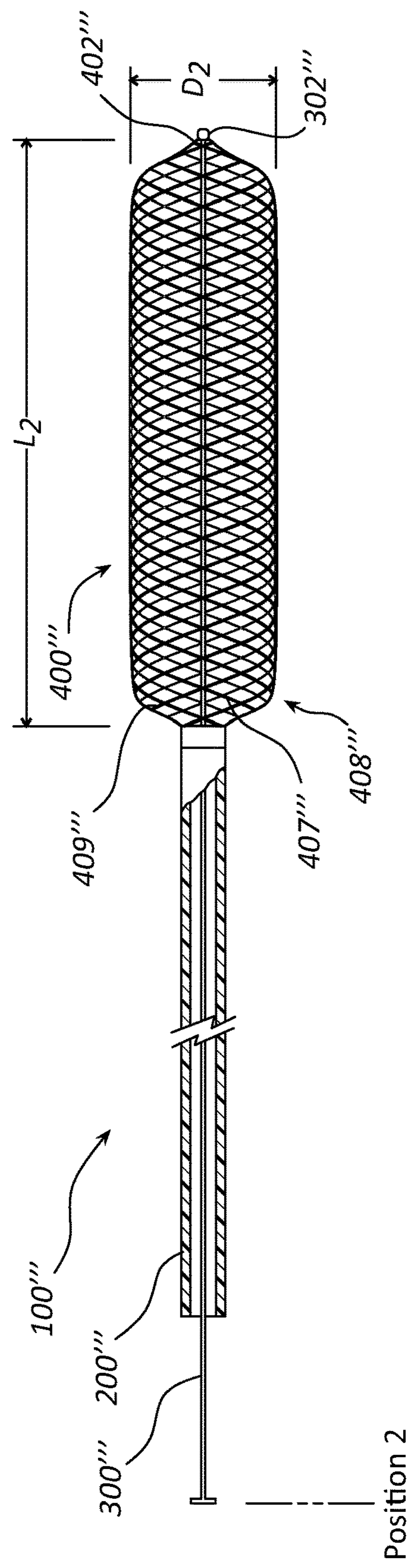
FIG. 11 shows the expandable braided stent of FIG. 10 in an expanded configuration.

FIGS. 10 and 11 illustrate a retrievable expandable stent delivery system 100''' that comprises a catheter 200''', a shaft 300''', and an expandable stent 400'''. The shaft 300''' may be coupled to the expandable stent 400'''. The shaft 300''' and the expandable stent 400''' may be disposed with the catheter 200''' and may be configured to slidably advance within the catheter 200'''. In some embodiments, the catheter 200''' and the shaft 300''' may be coupled to a handle (not shown) that may enable a user to manipulate the catheter 200''', the shaft 300''', and the expandable stent 400''' coupled to the shaft 300. In some embodiments, the retrievable expandable stent delivery system 100''' may be disposed within an outer catheter (not shown) and the retrievable expandable stent delivery system 100''' is slidable along the length of the outer catheter.

The expandable stent 400''' may comprise a plurality of filaments 408''' that extend from a distal end 402''' to a proximal end 404''' of the expandable stent 400'''. The number of filaments may vary in each embodiment. For example, the number of filaments 408''' may range between 5 filaments and 40 filaments. The filaments 408''' may be fabricated from a number of different materials, such as nitinol, a nitinol alloy, stainless steel, a stainless steel alloy, polyester multifilament, platinum alloys, or other composite materials, or a combination or blending of the material previously listed. The porosity of the expandable stent 400''' may be variable. For example, as the expandable stent 400''' expands, the porosity of the expandable stent 400''' may increase. In addition, the number of filaments 408''' may affect the porosity of the expandable stent 400'''. For example, the more filaments 408''' of the expandable stent 400''', the lower the porosity of the expandable stent 400'''. In some embodiments, the porosity of the expandable stent 400''' may range from 5 percent to 45 percent.

The filaments 408''' may be braided in a braiding pattern, thereby the expandable stent 400''' forms a mesh. For example, the filaments 408''' may be braided in a half-load braiding, a full load braiding pattern, a diamond braiding pattern, etc. The half load pattern comprises a first set of filaments 407''' (e.g., weft filaments) and a second set of filaments 409''' (warp filaments), wherein the first set of filaments 407''' rotate in an opposite direction as the second set of filaments 409'''. The first set of filaments 407''' is braided in an over-under pattern with the second set of filaments 409'''. In other words, a filament of the first set of filaments 407''' alternately goes over one filament of the second set of filaments 409''' under another filament of the second set of filaments 409''' and over another filament of the second set of filaments 409''', etc. until the filament reaches the opposite end (e.g., distal end 402''' or proximal end 404''') of the expandable sent 400'''.

In some embodiments, the braiding pattern is a full-load braiding pattern. Accordingly, the first set of filaments 407''' is braided in a two-over, two-under pattern with the second set of filaments 409'''. In other words, a filament of the first set of filaments 407''' alternately goes over two filaments of the second set of filaments 409''', under another two filaments of the second set of filaments 409''', over another two filaments of the second set of filaments 409''', etc. until the filament reaches the opposite end (e.g., distal end 402''' or proximal end 404''') of the expandable sent 400'''.

In some embodiments, the braiding pattern is a diamond braiding pattern. Accordingly, two filaments, side by side, of the first set of filaments 407''' are braided in a two-over, two-under pattern with the second set of filaments 409'''. In other words, two filaments, side by side, of the first set of filaments 407''' alternately go over two filaments of the second set of filaments 409''', under another two filaments of the second set of filaments 409''', over another two filaments of the second set of filaments 409''', etc. until the two filaments reaches the opposite end (e.g., distal end 402''' or proximal end 404''') of the expandable sent 400'''.

In some embodiments, the retrievable expandable stent 400''' may be coupled to the shaft 300'''. For example, the distal end 402''' of the expandable stent 400''' may be coupled to a distal end 302''' of the shaft 300'''. The proximal end 404''' of the expandable stent 400''' may be coupled to a distal end of the catheter 200'''. In some embodiments, the proximal end 404''' of the expandable stent 400''' may be attached to a marker band. In some embodiments, the relative movement between the distal end 402''' and the proximal end 404''' of the expandable stent 400''' is configured to expand the expandable stent 400'''. The expansion of the expandable stent 400''' may be controlled by a handle that may be manipulated by the user. The shaft 300''' is controlled by the handle via a lever, knob, or button. Manipulation of the level, knob, or button on the handle by the user shortens the shaft 300'' (or applies a proximally oriented force to the shaft 300''') which expands the expandable stent 400'''. Expansion of the expandable stent 400''' increases an outward radial force of the expandable stent 400''' to a vessel wall, which can lead to plaque fracturing in stenotic vessels plagued with atherosclerosis.

FIG. 10 illustrates the expandable stent 400''' in a collapsed configuration at a first diameter D1 and a first length L1 and FIG. 11 illustrates the expandable stent 400''' in an expanded configuration at a second diameter D2 and a second length L2. The second diameter D2 is greater than the first diameter D1 and second length L2 is less than the first length L1. Accordingly, as a user controls the handle to manipulate the position of the shaft 300''' and move the distal end 402''' of the expandable stent 400''' toward the proximal end 404''', the expandable stent 400''' expands. FIG. 10 illustrates the shaft 300''' at a first position and FIG. 11 illustrates the shaft 300''' at a second position, the change in position of the shaft 300''' changes the diameter of the expandable stent 400'''.

The filaments 408''' are configured to slide against each other and this enables the expandable stent 400''' to have additional flexibility in the expanded and collapsed configurations. The additional flexibility enables the expandable stent 400''' to conform to vessels of the patient, especially, intracranial vasculature.

Relative movement between the distal end 402''' and the proximal end 404''' may also collapse the expandable stent 400''' after the procedure is completed. The procedure after the expanded stent 400''' has achieved the desired outward expansion may be up to 60 minutes. In some embodiments, the expandable stent 400''' is removed after the procedure is completed. In other embodiments, the expandable stent 400''' may be detached from the shaft 300''' and left in a desired location within the patient's vasculature.

In some embodiments, the expandable stent 400''' may be drug-eluting. The expandable stent 400''' may include a drug covering or coating selected from the group of Everolimus, Paclitaxel, Siromlimus, Corolimus and any other related compounds, salts, moieties which potentially reduce the risk of thrombosis, lumen loss, and related challenges.

In some embodiments, the expandable stent 400''' may include radiopaque markers, such as platinum, gold, silver, or tantalum. In some embodiments, the expandable stent 400''' may be fabricated from bioabsorbable materials, such as magnesium based materials, polylactic acid-based (PLA's) polymers, and the like.

In some embodiments, the retrievable expandable stent delivery system 100''' further include a plurality of struts (similar to the struts discuss above) that are configured to help expand the expandable stent 400''' from the collapsed configuration to the expanded configuration. A first end of each strut may be coupled to the shaft 300''' and a second end of each strut may be coupled to the expandable stent 400'''. Longitudinal movement of the shaft 300 relative to the expandable stent 400''' may extend radially outward the plurality of struts and expand the retrievable expandable stent 400''' from the collapsed configuration to the expanded configuration. The struts are configured to help maintain the shape of the expandable stent 400''' in the expanded configuration and provides an outward radial force to the expandable stent 400'''.

Figure 12:
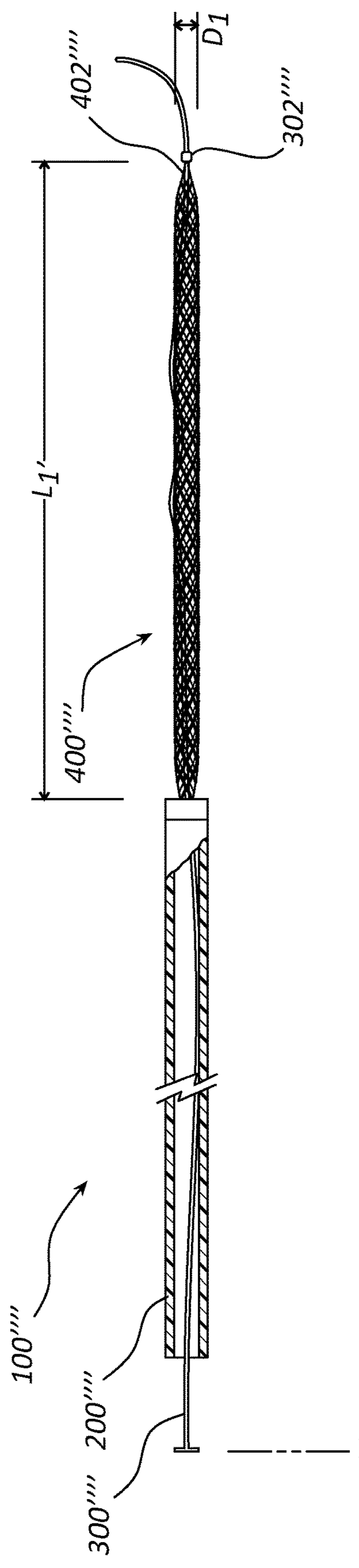
FIG. 12 shows an expandable braided stent in a collapsed configuration according to one embodiment.
Figure 13:
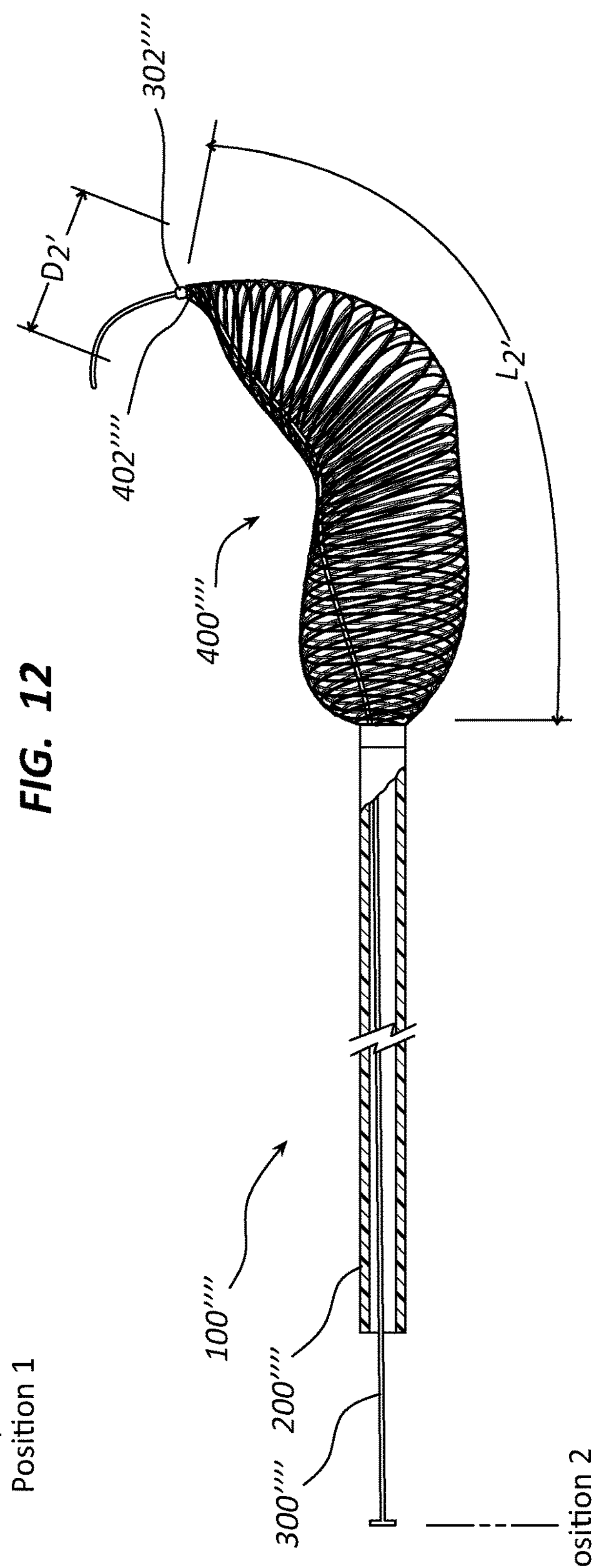
FIG. 13 shows the expandable braided stent of FIG. 12 in an expanded and curved configuration.

FIGS. 12 and 13 illustrate a retrievable expandable stent delivery system 100'''' that comprises a catheter 200'''', a shaft 300"", and an expandable stent 400"". The expandable stent 400"" is similar to the expandable stent 400''' of FIGS. 10 and 11, accordingly, duplicate features are not described below. The expandable stent 400"" comprises a plurality of filaments that are in a braiding pattern, such as the braiding patterns disclosed previously. FIG. 12 illustrates the expandable stent 400"" in a collapsed configuration at a first diameter D1' and at a first length L1' and FIG. 13 illustrates the expandable stent 400"" in an expanded configuration at a second diameter D2' and a second length L2'. The second diameter D2 is greater than the first diameter D1 and second length L2 is less than the first length L1.

In addition, the expandable stent 400"" is configured to bend and configure to parent vessel curvature during expansion, as illustrated in FIG. 13. A distal end 302"" of the shaft 300"" is configured to couple to a distal end 402"" of the expandable stent 400"". In addition, the shaft 300"" may be weaved into the expandable stent 400"". For example, FIG. 12 illustrates the shaft 300"" weaved out of and into the expandable stent 400"". Accordingly, when the user pulls on the shaft 300"", the expandable stent 400"" bends in a direction toward where the shaft 300"" is weaved within the expandable stent 400"". In some embodiments, the shaft 300"" may be weaved more than a single time. In some embodiments, the shaft 300"" is weaved out of and into the braid of the expandable stent 400"" two times. In some embodiments, the shaft 300"" is weaved out of and into the braid of the expandable stent 400"" three times. In some embodiments, the shaft 300"" is weaved along the entire lengths of the expandable stent 400"". The more the shaft 300"" is weaved into the expandable stent 400"", the greater the curvature of the expandable stent 300"".

In some embodiments, the shape of the expandable stent 400"" may be dependent upon how much of the expandable stent 400"" is deployed outside of the outer catheter (not shown). By not deploying the whole expandable stent 400"" outside the outer catheter, the amount of expandable stent 400"" that may be expanded is shortened.

The above note braided expandable stent may be used to treat intracranial atherosclerotic stenosis. A method of treating atherosclerotic stenosis may include placing a guide catheter system into a cervical and intracranial vasculature of a patient and delivering a microcatheter within to target vessel. The braided expandable stent may be deployed out of the microcatheter and across a target lumen for treating the stenosis in the collapsed configuration. A user may manipulate a handle of the system which manipulates the shaft and expands the braided expandable stent. The stent can remain expanded up to 60 min or at the discretion of the treating physician. The braided expandable stent applies an outward radial force to the vessel wall to dilate the subject vessel and treat the stenosis. The user may then collapse of the braided expandable stent through the handle. Once the device is collapsed, it can be re-sheathed in the microcatheter. The stent may or may not be non-detachable and may be or may not be fully retrieved at end of the procedure. The present disclosure is not limited to treat intracranial atherosclerotic stenosis, but may be used in different anatomic locations.

In some embodiments, the braided expandable stent may be a drug eluting stent. In some embodiments, the braided expandable stent may be a bioresorbable stent (bioresorbable stents/scaffold made either from magnesium based material) and/or Polylactic acid based polymers. In some embodiments, the braided expandable stent may be a bare-metal self-expanding stent and chimeric combinations or hybrids of the same, whereby the procedure time lowers the potential for vessel rupture.

In some embodiments, the braided expandable stent may comprise a coating, a marker, a system for marking or covering which is radiopaque wherein the coating, marker, system for marking or covering is disposed partially over a portion only of the surface of the braided expandable stent associated herewith. In some embodiments, Heparin and/or vasodilators may be injected during stent deployment to provide long lasting cerebral vasodilation for patients with multifocal and extensive ICAD.

In some embodiments, the method of treatment of ICAD secondary to another procedure with a non-detachable specialized stent. In some embodiments, the braided expandable stent is removable, after said stent is retrieved, nothing is left in the vessel, and yet long term restoration of the lumen diameter is achieved.

In some embodiments, the braided expandable stent is atraumatic, has a low profile, radiopaque, and has a robust geometry along with being removable. The braided expandable stent may further comprising at least a drug covering or coating selected from the group of Everolimus; Paclitaxel; Sirolimus; Corolimus and any related compounds, salts, moieties which potentially reduce risk of thrombosis, lumen loss and related challenges and/or the stent/stent-means is bioresorbable stents/scaffold made either from magnesium based material and/or Polylactic Acid-based (PLA's) (polymer), that could be implanted for ICAD as a treatment, which specifically designed high-radial force devices.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A method for deploying a retrievable expandable stent comprising:

placing a guide catheter system into a patient's vasculature;

delivering a microcatheter to an intracranial vessel of the patient to treat intracranial atherosclerotic stenosis;

deploying a braided expandable stent system out of a distal end of the microcatheter, the braided expandable stent system comprising:

a handle comprising a manipulable control component;

a shaft comprising a proximal end and a distal end; and a braided expandable stent with a proximal end and a distal end, wherein the distal end of the shaft is coupled to the distal end of the braided expandable stent and the shaft is disposed within the expandable stent, and wherein the shaft is coupled to the handle and manipulation of the manipulable control component shortens or lengthens a length of the shaft which expands or collapses the braided expandable stent, radially expanding the braided expandable stent providing an outward radial force to a vessel wall to dilate the vessel wall and cracking plaque in the intracranial vessel;

manipulating the manipulable control component on the handle to adjust an amount of the outward radial force of the braided expandable stent; and applying the outward radial force to the vessel wall for up to 60 minutes;

wherein the shaft is woven out of and into the braided expandable stent in at least one location such that the shaft is external to an external surface of the expandable stent, and pulling the shaft to bend the braided expandable stent in a direction the shaft is weaved out of and into the braided expandable stent.

2. The method of claim 1, further comprising collapsing the braided expandable stent and resheathing the braided expandable stent into the microcatheter.

3. The method of claim 1, wherein the braided expandable stent elutes a drug.

4. The method of claim 1, wherein the braided expandable stent is fabricated from a bioresorbable material.

5. The method of claim 1, further comprising injecting Heparin and/or vasodilators during stent deployment.

6. The method of claim 1, wherein the braided expandable stent comprises a radiopaque marker.

7. The method of claim 1, wherein the outward radial force is between 0.00590 and 0.0090 Newtons/mm.

8. The method of claim 1, wherein the outward radial force is applied to the vessel wall for 15 to 30 minutes.

9. The method of claim 1, wherein the manipulable control component is a knob.

* * * * *